(12) United States Patent
Xu et al.

(10) Patent No.: US 8,945,934 B2
(45) Date of Patent: Feb. 3, 2015

(54) POTENTIOMETRIC TITRATION METHOD FOR MEASURING CONCENTRATION OF ACID MIXTURE OF ALUMINUM ETCHANT

(75) Inventors: Rui Xu, Shenzhen (CN); Weiwei Zhang, Shenzhen (CN); Jingming Wu, Shenzhen (CN); Honghui Zhu, Shenzhen (CN); Li Wang, Shenzhen (CN); Xiaobo He, Shenzhen (CN); Hongqing Huang, Shenzhen (CN)

(73) Assignee: Shenzhen China Star Optoelectronics Technology Co., Ltd., Shenzhen, Guangdong Province (CN)

( * ) Notice: Subject to any disclaimer, the term of this patent is extended or adjusted under 35 U.S.C. 154(b) by 132 days.

(21) Appl. No.: 13/699,638

(22) PCT Filed: Aug. 23, 2012

(86) PCT No.: PCT/CN2012/080481
§ 371 (c)(1),
(2), (4) Date: Nov. 22, 2012

(87) PCT Pub. No.: WO2014/023045
PCT Pub. Date: Feb. 13, 2014

(65) Prior Publication Data
US 2014/0045271 A1    Feb. 13, 2014

(51) Int. Cl.
*G01N 31/16* (2006.01)
*G01N 31/00* (2006.01)
(52) U.S. Cl.
CPC .................................... *G01N 31/164* (2013.01)
USPC ........................................................ 436/100

(58) Field of Classification Search
CPC ..... G01N 31/164; G01N 31/162; G01N 31/16
USPC .......................................................... 436/100
See application file for complete search history.

(56) References Cited

FOREIGN PATENT DOCUMENTS

| CN | 1379288 A | 11/2002 |
|----|-----------|---------|
| KR | 10-0816657 B1 | 3/2008 |
| WO | 99/12026 A1 | 3/1999 |

OTHER PUBLICATIONS

Machine Translation of KR 10-0816657, Youn Suk Hwan, The method for quantitative analysis of the mixed acid liquid, p. 1-11.*

* cited by examiner

*Primary Examiner* — Christine T Mui
(74) *Attorney, Agent, or Firm* — Cheng-Ju Chiang

(57) ABSTRACT

The present invention provides a potentiometric titration method for measuring concentration of acid mixture of aluminum etchant, which prepares identified potassium hydroxide-ethanol solution or sodium hydroxide-ethanol solution as a titrant and uses a monohydric alcohol and a diol as an anhydrous medium for the acid mixture of aluminum etchant to carry out titration of the acid mixture of aluminum etchant so as to realize measurement of concentration of each acid contained in the acid mixture of aluminum etchant through a one-stage process of potentiometric titration thereby reducing the complication of operation of inspection and uncertainty of inspection result and achieving the purposes of carrying out inspections with high precision and high performance. The method can efficiently and accurately measure the concentrations of nitric acid, phosphoric acid, and acetic acid contained in the acid mixture of aluminum etchant.

11 Claims, 3 Drawing Sheets

POTENTIOMETRIC TITRATION METHOD FOR MEASURING CONCENTRATION OF ACID MIXTURE OF ALUMINUM ETCHANT

BACKGROUND OF THE INVENTION

1. Field of the Invention

The present invention relates to the field of etchant solution, and in particular to a potentiometric titration method for measuring concentration of acid mixture of aluminum etchant.

2. The Related Arts

Wet etching processes are core processes of applying acid corrosive solutions to patternize metal layers in order to form a gate terminal, a source-drain terminal, and a pixel electrode in the fabrication of a thin-film transistor (TFT). Aluminum and molybdenum are conductive materials that commonly used to form the gate terminal and an acid etchant used may be composed of a variety of different acids, but in most cases, a mixture of strong acids (such as phosphoric acid, nitric acid, and glacial acetic acid) is applied to dissolve and oxidize/reduce aluminum and molybdenum so as to realize patternization of the gate layer.

A composition of acid mixture for aluminum etchants generally comprise phosphoric acid (70%-72%), nitric acid (1.8%-2.0%), and glacial acetic acid (8.0%-10%), among which nitric acid functions to provide $H_3O+$ to oxidize metal aluminum for effecting wet etching. Phosphate provides phosphate group to form a complex with oxidized metal so as to dissolve metal oxides. Glacial acetic acid adheres to a surface of reactants to reduce viscosity of the etchant for increasing permeability thereof and adjusting etching rate. Therefore, well controlling concentrations of various acids contained in the etchant solution is vital to the adjustment of etching rate and formation of etched configuration.

Based on the acid-base proton theory, the acidic or basic strength that a substance exhibits in a solution is not only pertaining to the nature of the substance but also pertaining to the property of the solution. Measurement of acidic components in an aqueous solution through titration can only be done when Pka between different acids is as high as 5. Thus, it is generally impossible to distinguish nitric acid (of which PKa is −1.32) from the first dissociation of phosphoric acid (of which $PKa_1$ is 1.96) or to distinguish acetic acid (of which PKa is 4.73) from the second dissociation of phosphoric acid (of which $PKa_2$ is 7.12). Due to the so called "leveling effect" of aqueous solutions, distinction of various acids in an acid mixture can only be done with a multiple-stage process or be done in a non-aqueous solution.

A potentiometric titration method determines the titration end point through detecting an abrupt potential change during titrating. This method shows high sensitivity and accuracy and may realize automatic and successive titration and is thus of wide applications. Existing approaches of acid mixture in potentiometric titration are generally effected with a two-stage process applied in combination with appropriate non-aqueous solvents. As shown in FIG. 1A, in the first stage, an ethanol solution of tetrabutylammonium bromide is used as a titrant with an anhydrous ethanol as a solvent, or an isopropanol solution of potassium hydroxide (KOH) is used as a titrant with a methanol as solvent to titrate nitric acid contained in an acid mixture. As shown in FIG. 1B, in the second stage, a sodium hydroxide aqueous solution is used as a titrant with a saturated sodium chloride solution as a solvent to titrate phosphoric acid and glacial acetic acid contained in the acid mixture. The titration process generates two end points, of which the first end point is associated with nitric acid and the first hydrogen ion of phosphoric acid and the second end point is associated with the second hydrogen ion of phosphoric acid and acetic acid. Through an automatic computation process, the contents of the three acids can be obtained. These conventional approaches are carried out with a two-stage process and computation and the titration operation is complicated and tedious and requires various titrants and solvents, which would lead to increased uncertainty and thereby reduce the accuracy and repeatability of the result of titration.

SUMMARY OF THE INVENTION

An object of the present invention is to provide a potentiometric titration method for measuring acid mixture of aluminum etchant, which adopts a one-stage potentiometric titration of acid mixture in a non-aqueous solvent to substitute the conventional two-stage potentiometric titration of acid mixture for the purposes of simplifying the operation process of inspections, reducing errors of inspection results, improving accuracy of inspections, and saving operation time.

To achieve the object, the present invention provides a potentiometric titration method for measuring concentration of acid mixture of aluminum etchant, which comprises the following steps:

Step 1: preparing an alkali-ethanol solution having a concentration of 0.8-1.2 mol/L with alkali as solute and anhydrous ethanol as solvent;

Step 2: setting the alkali-ethanol solution so prepared still and precipitated for 20-30 days and afterwards, extracting upper clear liquid in the alkali-ethanol solution;

Step 3: diluting the upper clear liquid with anhydrous ethanol to a concentration of 0.1-0.2 mol/L and performing a vacuum-filtrating process to obtain a titrative alkali-ethanol solution;

Step 4: baking potassium hydrogen phthalate in an oven at 105° C. for 10-12 hours and then placing the potassium hydrogen phthalate in a dryer for cooling for at least 1 hour;

Step 5: with the potassium hydrogen phthalate obtained above as solute and distilled water as solvent, preparing a potassium hydrogen phthalate solution in an automatic potentiometric-titrator by weighing an appropriate amount of the potassium hydrogen phthalate obtained above and added with the distilled water, the result of weighing the potassium hydrogen phthalate being as precise as 0.1 mg;

Step 6: dripping the titrative alkali-ethanol solution in the potassium hydrogen phthalate solution by using the automatic potentiometric-titrator to achieve a first end point, and computing concentration of the titrative alkali-ethanol solution;

Step 7: repeating Step 6 twice and computing an average of the concentrations of the titrative alkali-ethanol solution for the three titrations in order to determine an actual concentration of the titrative alkali-ethanol solution;

Step 8: providing an acid mixture of aluminum etchant, which includes an acid mixture sample comprising nitric acid, phosphoric acid, and acetic acid and adding a first solvent and a second solvent in the acid mixture sample and uniformly stirring to obtain an acid mixture solution of aluminum etchant, the first solvent being monohydric alcohol and the second solvent being diol;

Step 9: dripping the titrative alkali-ethanol solution in the acid mixture of aluminum etchant by using the automatic potentiometric-titrator to achieve a first, a second and a third equivalence points and computing concentrations of nitric acid, phosphoric acid, and acetic acid contained in the acid mixture of aluminum etchant according to amounts of consumption of the titrative alkali-ethanol solution when the first, second, and third equivalence points occur by applying the following formulas:

$$m_{HNO_3}\% = V_{EP1} \times C \times M_{HNO_3}/m;$$

$$m_{H_3PO_4}\% = V_{(EP2-EP1)} \times C \times M_{H_3PO_4}/m; \text{ and}$$

$$m_{HAC}\% = V_{(EP3-EP2)} \times C \times M_{HAC}/m;$$

wherein C is concentration of the alkali-ethanol solution; $V_{EP1}$ is the volume of the alkali-ethanol solution consumed at the first equivalence point; $V_{(EP2-EP1)}$ is difference between volumes of the alkali-ethanol solution consumed at the second and the first equivalence points; $V_{(EP3-EP3)}$ is difference between volumes of the alkali-ethanol solution consumed at the third and the second equivalence points; m represents the mass of the acid mixture of aluminum etchant used; and M is molar mass of each one of the acids; and Step 10: repeating Step 9 twice and computing averages of the concentrations of nitric acid, phosphoric acid, and acetic acid contained in the acid mixture of aluminum etchant for the three measurements to determine actual concentrations of nitric acid, phosphoric acid, and acetic acid.

The alkali comprises potassium hydroxide having an AR concentration greater than or equal to 85%.

The monohydric alcohol comprises methanol or ethanol.

The diol comprises glycol, 1,2-propanediol, or 1,4-butanediol.

The first solvent and the second solvent have a volume ratio therebetween of 3:1-3:5.

Sum of volumes of the first and second solvents is 200-400 times of mass of the acid mixture sample of aluminum etchant.

The alkali comprises sodium hydroxide having an AR concentration greater than or equal to 96%.

In Step (1), the alkali-ethanol solution has a concentration of 1 mol/L.

In Step (2), the alkali-ethanol solution is set still and precipitated for 30 days.

In Step (4), potassium hydrogen phthalate is baked for a period of 12 hours.

The present invention also provides a potentiometric titration method for measuring concentration of acid mixture of aluminum etchant, which comprises the following steps:

Step 1: preparing an alkali-ethanol solution having a concentration of 0.8-1.2 mol/L with alkali as solute and anhydrous ethanol as solvent;

Step 2: setting the alkali-ethanol solution so prepared still and precipitated for 20-30 days and afterwards, extracting upper clear liquid in the alkali-ethanol solution;

Step 3: diluting the upper clear liquid with anhydrous ethanol to a concentration of 0.1-0.2 mol/L and performing a vacuum-filtrating process to obtain a titrative alkali-ethanol solution;

Step 4: baking potassium hydrogen phthalate in an oven at 105° C. for 10-12 hours and then placing the potassium hydrogen phthalate in a dryer for cooling for at least 1 hour;

Step 5: with the potassium hydrogen phthalate obtained above as solute and distilled water as solvent, preparing a potassium hydrogen phthalate solution in an automatic potentiometric-titrator by weighing an appropriate amount of the potassium hydrogen phthalate obtained above and added with the distilled water, the result of weighing the potassium hydrogen phthalate being as precise as 0.1 mg;

Step 6: dripping the titrative alkali-ethanol solution in the potassium hydrogen phthalate solution by using the automatic potentiometric-titrator to achieve a first end point, and computing concentration of the titrative alkali-ethanol solution;

Step 7: repeating Step (6) twice and computing an average of the concentration of the titrative alkali-ethanol solution for the three titrations in order to determine an actual concentration of the titrative alkali-ethanol solution;

Step 8: providing an acid mixture of aluminum etchant, which includes an acid mixture sample comprising nitric acid, phosphoric acid, and acetic acid and adding a first solvent and a second solvent in the acid mixture sample and uniformly stirring to obtain an acid mixture solution of aluminum etchant, the first solvent being monohydric alcohol and the second solvent being diol;

Step 9: dripping the titrative alkali-ethanol solution in the acid mixture of aluminum etchant by using the automatic potentiometric-titrator to achieve a first, a second and a third equivalence points and computing concentrations of nitric acid, phosphoric acid, and acetic acid contained in the acid mixture of aluminum etchant according to amounts of consumption of the titrative alkali-ethanol solution when the first, second, and third equivalence points occur by applying the following formulas:

$$m_{HNO_3}\% = V_{EP1} \times C \times M_{HNO_3}/m;$$

$$m_{H_3PO_4}\% = V_{(EP2-EP1)} \times C \times M_{H_3PO_4}/m; \text{ and}$$

$$m_{HAC}\% = V_{(EP3-EP2)} \times C \times M_{HAC}/m;$$

wherein C is concentration of the alkali-ethanol solution; $V_{EP1}$ is the volume of the alkali-ethanol solution consumed at the first equivalence point; $V_{(EP2-EP1)}$ is difference between volumes of the alkali-ethanol solution consumed at the second and the first equivalence points; $V_{(EP3-EP3)}$ is difference between volumes of the alkali-ethanol solution consumed at the third and the second equivalence points; m represents the mass of the acid mixture of aluminum etchant used; and M is molar mass of each one of the acids; and Step 10: repeating Step (9) twice and computing averages of the concentrations of nitric acid, phosphoric acid, and acetic acid contained in the acid mixture of aluminum etchant for the three measurements to determine actual concentrations of nitric acid, phosphoric acid, and acetic acid;

wherein the alkali comprises potassium hydroxide having an AR concentration greater than or equal to 85%;

wherein the monohydric alcohol comprises methanol or ethanol;

wherein the diol comprises glycol, 1,2-propanediol, or 1,4-butanediol;

wherein the first solvent and the second solvent have a volume ratio therebetween of 3:1-3:5;

wherein sum of volumes of the first and second solvents is 200-400 times of mass of the acid mixture sample of aluminum etchant;

wherein in Step (1), the alkali-ethanol solution has a concentration of 1 mol/L;

wherein in Step (2), the alkali-ethanol solution is set still and precipitated for 30 days; and wherein in Step (4), potassium hydrogen phthalate is baked for a period of 12 hours.

The efficacy of the present invention is that the present invention provides a potentiometric titration method for measuring concentration of acid mixture of aluminum etchant, which uses a monohydric alcohol and a diol as an anhydrous medium for the acid mixture of aluminum etchant and uses potassium hydroxide-ethanol solution or sodium hydroxide-ethanol solution as a titrant to carry out titration of the acid mixture of aluminum etchant for measurement of concentration of each acid contained in the acid mixture of aluminum etchant through a one-stage process of potentiometric titration thereby reducing the complication of operation of inspection and uncertainty of inspection result and achieving the purposes of carrying out inspections with high precision and high performance. The method can efficiently and accurately measure the concentrations of nitric acid, phosphoric acid, and acetic acid contained in the acid mixture of aluminum etchant and is vital to the adjustment of etching rate and formation of excellent gate terminal configuration. This method can be widely applicable in the TFT industry.

For better understanding of the features and technical contents of the present invention, reference will be made to the following detailed description of the present invention and the attached drawings. However, the drawings are provided for the purposes of reference and illustration and are not intended to impose undue limitations to the present invention.

BRIEF DESCRIPTION OF THE DRAWINGS

The technical solution, as well as beneficial advantages, of the present invention will be apparent from the following detailed description of an embodiment of the present invention, with reference to the attached drawings. In the drawings.

DETAILED DESCRIPTION OF THE PREFERRED EMBODIMENTS

To further expound the technical solution adopted in the present invention and the advantages thereof, a detailed description is given to a preferred embodiment of the present invention and the attached drawings.

Figure 1A:
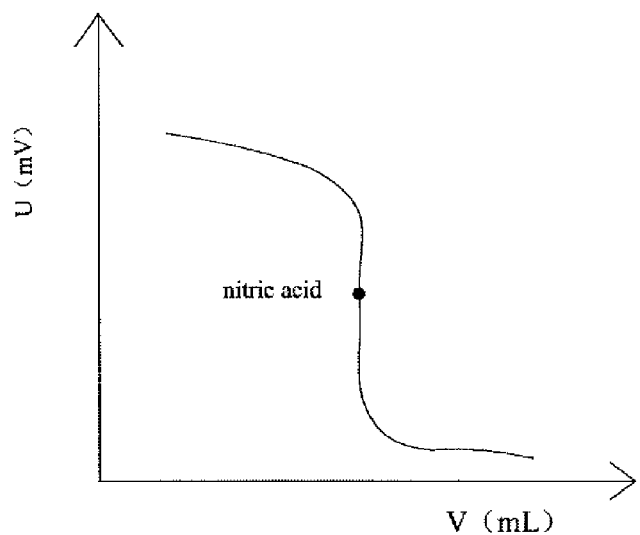
FIGS. 1A and 1B show titration plots of conventional two-stage titration of acid mixture of aluminum etchant.
Figure 1B:
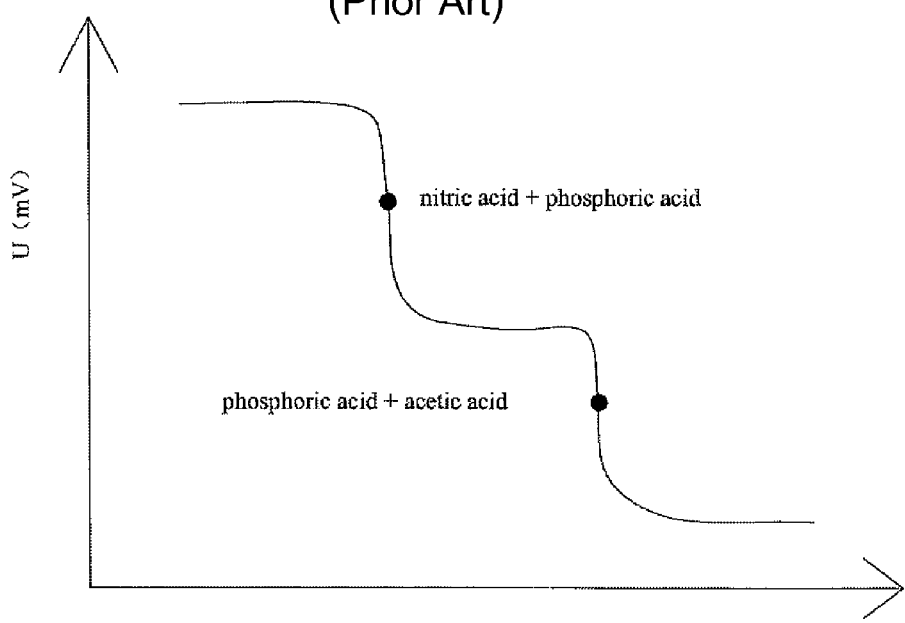
Figure 2:
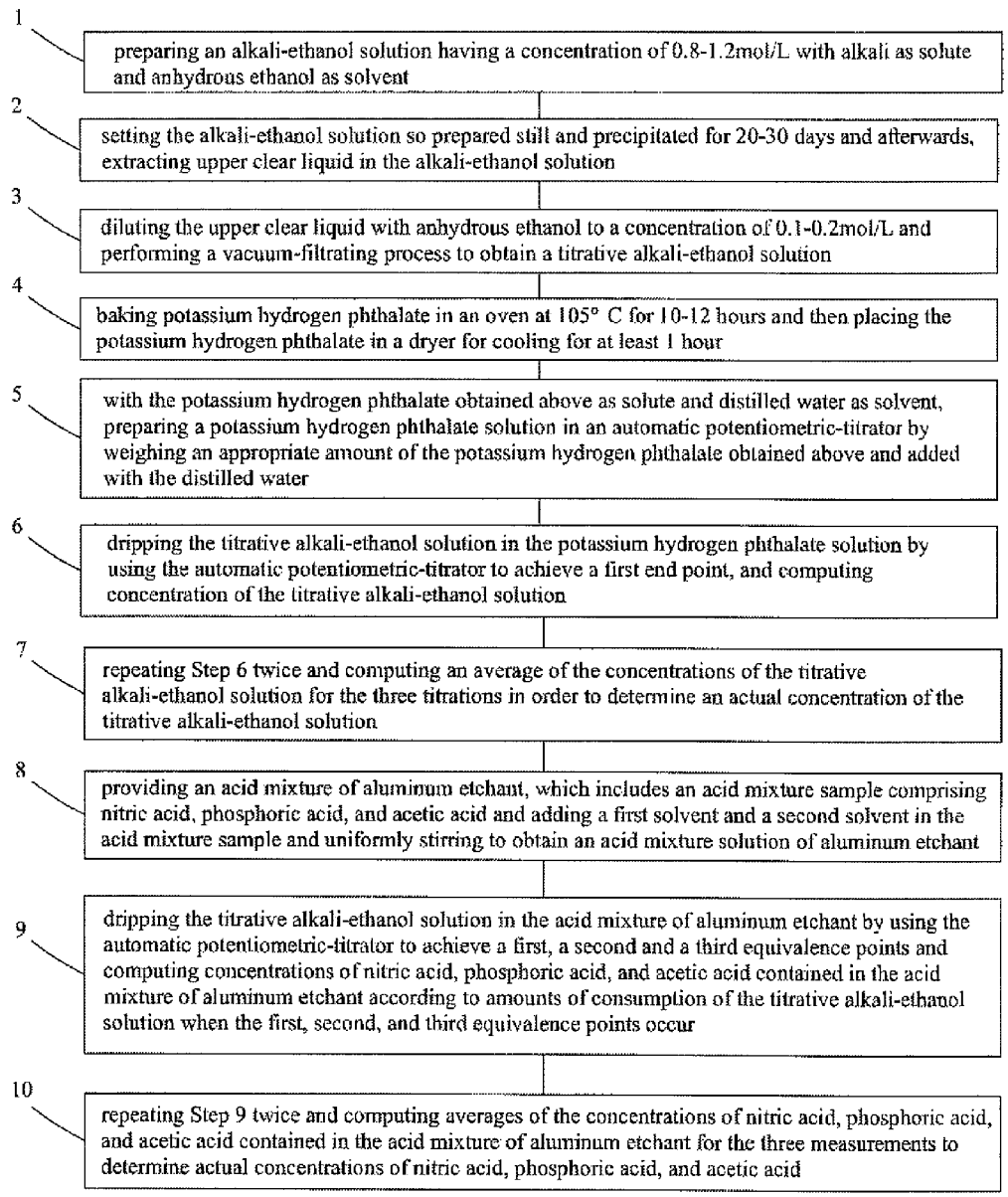
FIG. 2 is a flow chart showing a potentiometric titration method for measuring concentration of acid mixture of aluminum etchant.
Figure 3:
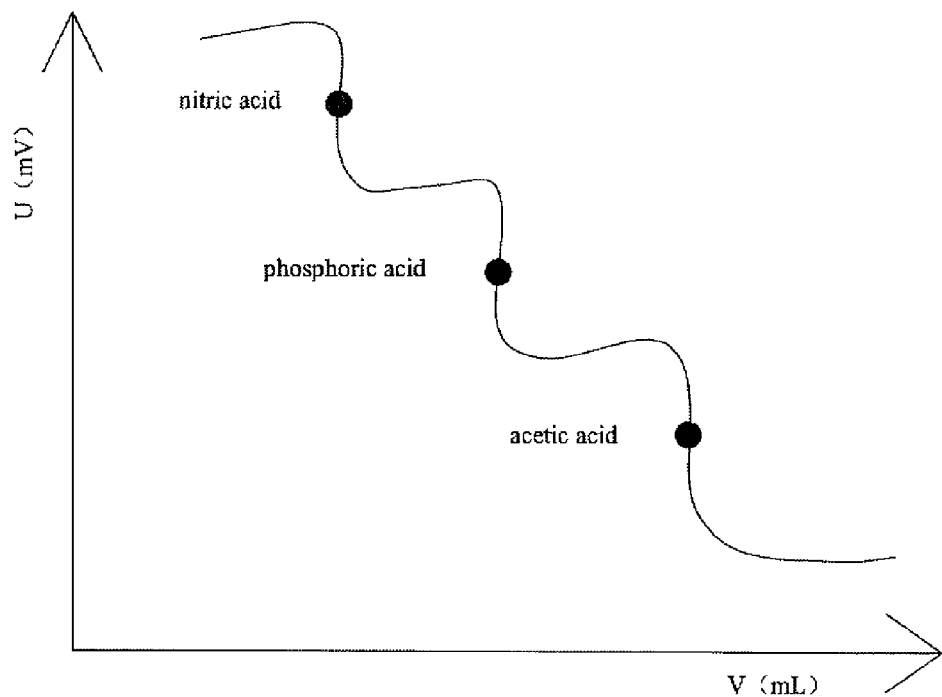
FIG. 3 shows a titration plot of the potentiometric titration method for measuring concentration of acid mixture of aluminum etchant according to the present invention.

Referring to FIGS. 2 and 3, the present invention provides a potentiometric titration method for measuring concentration of acid mixture of aluminum etchant. The potentiometric titration method for measuring concentration of acid mixture of aluminum etchant according to the present invention uses a monohydric alcohol and a diol as an anhydrous medium for the acid mixture of aluminum etchant and uses an alkali-ethanol solution as a titrant to measure the concentration of each acid contained in the acid mixture of aluminum etchant through a one-stage process of potentiometric titration. The alkali used can be potassium hydroxide that has an analytical reagent (AR) concentration of greater than or equal to 85%. The alkali can alternatively be sodium hydroxide having an AR concentration greater than or equal to 96%.

A description will be given by taking potassium hydroxide as an example:

Step 1: preparing a potassium hydroxide-ethanol solution having a concentration of 0.8-1.2 mol/L with potassium hydroxide as solute and anhydrous ethanol as solvent.

An electronic balance is used to precise weigh a predetermined amount of potassium hydroxide (AR content being greater than or equal to 85%), which is dissolved with anhydrous ethanol to prepare the KOH-ethanol solution of a concentration of 1 mol/L.

Step 2: setting the potassium hydroxide-ethanol solution so prepared still and precipitated for 20-30 days and afterwards, extracting upper clear liquid in the alkali-ethanol solution.

Preferably, the alkali-ethanol solution is set still for precipitation for a period of 30 days.

Step 3: diluting the upper clear liquid with anhydrous ethanol to a concentration of 0.1-0.2 mol/L and performing a vacuum-filtrating process to obtain a titrative potassium hydroxide-ethanol solution.

Preferably, the dilution with anhydrous ethanol is made to a concentration of 0.1 mol/L or 0.2 mol/L.

Step 4: baking potassium hydrogen phthalate in an oven at 105° C. for 10-12 hours and then placing the potassium hydrogen phthalate in a dryer for cooling for at least 1 hour.

A large amount of potassium hydrogen phthalate is prepared and deposited in an oven at 105° C. for baking 12 hours and then, the potassium hydrogen phthalate is placed in a dryer to cool down for at least 1 hour.

Step 5: with the potassium hydrogen phthalate obtained above as solute and distilled water as solvent, preparing a potassium hydrogen phthalate solution in an automatic potentiometric-titrator by precisely weighing an appropriate amount of the potassium hydrogen phthalate obtained above and added with the distilled water.

A precisely weighed amount of potassium hydrogen phthalate (0.2-0.3 g) is prepared (with precision as good as 0.1 mg) and placed in a titration beaker and added with a proper amount of distilled water to have electrodes covered. Completely dissolution is achieved through stirring in room temperature to obtain the potassium hydrogen phthalate solution.

Step 6: dripping the titrative potassium hydroxide-ethanol solution in the potassium hydrogen phthalate solution by using an automatic potentiometric-titrator to achieve a first end point, and computing the concentration of the titrative potassium hydroxide-ethanol solution Based on the amount of potassium hydrogen phthalate used and the volume of the titrative potassium hydroxide solution consumed when the first end point occurs, the concentration of the titrative potassium hydroxide can be computed.

Step 7: repeating Step 6 twice and computing an average of the concentrations of the titrative alkali-ethanol solution for the three titrations in order to determine an actual concentration of the titrative alkali-ethanol solution.

Step 8: providing an acid mixture of aluminum etchant, which includes an acid mixture sample comprising nitric acid, phosphoric acid, and acetic acid and adding a first solvent and a second solvent in the acid mixture sample and uniformly stirring to obtain an acid mixture solution of aluminum etchant.

The acid mixture of aluminum etchant that includes nitric acid, phosphoric acid, and acetic acid are precisely weighed for m (g) and a volume V1 (mL) of the first solvent and a volume V2 (mL) of the second solvent are added and are uniformly stirred to obtain the acid mixture of aluminum etchant.

The first solvent comprises monohydric alcohol, which is preferably methanol or ethanol. The second solvent comprises diol, which is preferably glycol, 1,2-propanediol, or 1,4-butanediol. The first solvent and the second solvent have a volume ratio V1:V2 that is between 3:1-3:5. The sum of the volumes of the first and second solvents, V1+V2, is 200-400 times of the contents, m (g), of the acid mixture sample of aluminum etchant.

Step 9: dripping the titrative potassium hydroxide-ethanol solution in the acid mixture of aluminum etchant by using an automatic potentiometric-titrator to achieve a first, a second and a third equivalence points and computing concentrations of nitric acid, phosphoric acid, and acetic acid contained in the acid mixture of aluminum etchant according to amounts of consumption of the titrative potassium hydroxide-ethanol solution when the first, second, and third equivalence points occur by applying the following formulas:

$$m_{HNO_3}\% = V_{EP1} \times C \times M_{HNO_3}/m;$$

$$m_{H_3PO_4}\% = V_{(EP2-EP1)} \times C \times M_{H_3PO_4}/m, \text{ and}$$

$$m_{HAC}\% = V_{(EP3-EP2)} \times C \times M_{HAC}/m;$$

wherein C is concentration of the potassium hydroxide-ethanol solution; $V_{EP1}$ is the volume of the potassium hydroxide-ethanol solution consumed at the first equivalence point; $V_{(EP2-EP1)}$ is difference between volumes of the potassium hydroxide-ethanol solution consumed at the second and the first equivalence points; $V_{(EP3-EP3)}$ is difference between volumes of the potassium hydroxide-ethanol solution consumed at the third and the second equivalence points; m represents the mass of the acid mixture of aluminum etchant used; and M is molar mass of each one of the acids.

Steps 10: repeating Step 9 twice and computing averages of the concentrations of nitric acid, phosphoric acid, and acetic acid contained in the acid mixture of aluminum etchant for the three measurements to determine actual concentrations of nitric acid, phosphoric acid, and acetic acid in the acid mixture of aluminum etchant.

In summary, the present invention provides a potentiometric titration method for measuring concentration of acid mixture of aluminum etchant, which uses a monohydric alcohol and a diol as an anhydrous medium for the acid mixture of aluminum etchant and uses potassium hydroxide-ethanol solution or sodium hydroxide-ethanol solution as a titrant to carry out titration of the acid mixture of aluminum etchant for measurement of concentration of each acid contained in the acid mixture of aluminum etchant through a one-stage process of potentiometric titration thereby so as to reduce the complication of operation of inspection and uncertainty of inspection result and achieving the purposes of carrying out inspections with high precision and high performance. The method can efficiently and accurately measure the concentrations of nitric acid, phosphoric acid, and acetic acid contained in the acid mixture of aluminum etchant and is vital to the adjustment of etching rate and formation of excellent gate terminal configuration. This method can be widely applicable in the TFT industry. This method reduces the complication of operation of inspection and uncertainty of inspection result and achieving the purposes of carrying out inspections with high precision and high performance.

Based on the description given above, those having ordinary skills of the art may easily contemplate various changes and modifications of the technical solution and technical ideas of the present invention and all these changes and modifications are considered within the protection scope of right for the present invention.

What is claimed is:

1. A potentiometric titration method for measuring concentration of acid mixture of aluminum etchant, comprising the following steps:
    (1) preparing an alkali-ethanol solution having a concentration of 0.8-1.2 mol/L with alkali as solute and anhydrous ethanol as solvent;
    (2) setting the alkali-ethanol solution so prepared still and precipitated for 20-30 days and afterwards, extracting upper clear liquid in the alkali-ethanol solution;
    (3) diluting the upper clear liquid with anhydrous ethanol to a concentration of 0.1-0.2 mol/L and performing a vacuum-filtrating process to obtain a titrative alkali-ethanol solution;
    (4) baking potassium hydrogen phthalate in an oven at 105° C. for 10-12 hours and then placing the potassium hydrogen phthalate in a dryer for cooling for at least 1 hour;
    (5) with the potassium hydrogen phthalate obtained above as solute and distilled water as solvent, preparing a potassium hydrogen phthalate solution in an automatic potentiometric-titrator by weighing an appropriate amount of the potassium hydrogen phthalate obtained above and added with the distilled water, the result of weighing the potassium hydrogen phthalate being as precise as 0.1 mg;
    (6) dripping the titrative alkali-ethanol solution in the potassium hydrogen phthalate solution by using the automatic potentiometric-titrator to achieve a first end point, and computing concentration of the titrative alkali-ethanol solution;
    (7) repeating Step (6) twice and computing an average of the concentrations of the titrative alkali-ethanol solution for the three titrations in order to determine an actual concentration of the titrative alkali-ethanol solution;
    (8) providing an acid mixture of aluminum etchant, which includes an acid mixture sample comprising nitric acid, phosphoric acid, and acetic acid and adding a first solvent and a second solvent in the acid mixture sample and uniformly stirring to obtain an acid mixture solution of aluminum etchant, the first solvent being monohydric alcohol and the second solvent being diol;
    (9) dripping the titrative alkali-ethanol solution in the acid mixture of aluminum etchant by using the automatic potentiometric-titrator to achieve a first, a second and a third equivalence points and computing concentrations of nitric acid, phosphoric acid, and acetic acid contained in the acid mixture of aluminum etchant according to amounts of consumption of the titrative alkali-ethanol solution when the first, second, and third equivalence points occur by applying the following formulas:

$$m_{HNO_3}\% = V_{EP1} \times C \times M_{HNO_3}/m;$$

$$m_{H_3PO_4}\% = V_{(EP2-EP1)} \times C \times M_{H_3PO_4}/m; \text{ and}$$

$$m_{HAC}\% = V_{(EP3-EP2)} \times C \times M_{HAC}/m;$$

wherein C is concentration of the alkali-ethanol solution; $V_{EP1}$ is the volume of the alkali-ethanol solution consumed at the first equivalence point; $V_{(EP2-EP1)}$ is difference between volumes of the alkali-ethanol solution consumed at the second and the first equivalence points; $V_{(EP3-EP2)}$ is difference between volumes of the alkali-ethanol solution consumed at the third and the second equivalence points; m represents the mass of the acid mixture of aluminum etchant used; and M is molar mass of each one of the acids; and
    (10) repeating Step (9) twice and computing averages of the concentrations of nitric acid, phosphoric acid, and acetic acid contained in the acid mixture of aluminum etchant for the three measurements to determine actual concentrations of nitric acid, phosphoric acid, and acetic acid.

2. The potentiometric titration method for measuring concentration of acid mixture of aluminum etchant as claimed in claim 1, wherein the alkali comprises potassium hydroxide having an analytical reagent (AR) concentration greater than or equal to 85%.

3. The potentiometric titration method for measuring concentration of acid mixture of aluminum etchant as claimed in claim 1, wherein the monohydric alcohol comprises methanol or ethanol.

4. The potentiometric titration method for measuring concentration of acid mixture of aluminum etchant as claimed in claim 1, wherein the diol comprises glycol, 1,2-propanediol, or 1,4-butanediol.

5. The potentiometric titration method for measuring concentration of acid mixture of aluminum etchant as claimed in claim 1, wherein the first solvent and the second solvent have a volume ratio therebetween of 3:1-3:5.

6. The potentiometric titration method for measuring concentration of acid mixture of aluminum etchant as claimed in claim 1, wherein sum of volumes of the first and second solvents is 200-400 times of mass of the acid mixture sample of aluminum etchant.

7. The potentiometric titration method for measuring concentration of acid mixture of aluminum etchant as claimed in claim 1, wherein the alkali comprises sodium hydroxide having an analytical reagent (AR) concentration greater than or equal to 96%.

8. The potentiometric titration method for measuring concentration of acid mixture of aluminum etchant as claimed in claim 1, wherein in Step (1), the alkali-ethanol solution has a concentration of 1 mol/L.

9. The potentiometric titration method for measuring concentration of acid mixture of aluminum etchant as claimed in claim 1, wherein in Step (2), the alkali-ethanol solution is set still and precipitated for 30 days.

10. The potentiometric titration method for measuring concentration of acid mixture of aluminum etchant as claimed in claim 1, wherein in Step (4), potassium hydrogen phthalate is baked for a period of 12 hours.

11. A potentiometric titration method for measuring concentration of acid mixture of aluminum etchant, comprising the following steps:
  (1) preparing an alkali-ethanol solution having a concentration of 0.8-1.2 mol/L with alkali as solute and anhydrous ethanol as solvent;
  (2) setting the alkali-ethanol solution so prepared still and precipitated for 20-30 days and afterwards, extracting upper clear liquid in the alkali-ethanol solution;
  (3) diluting the upper clear liquid with anhydrous ethanol to a concentration of 0.1-0.2 mol/L and performing a vacuum-filtrating process to obtain a titrative alkali-ethanol solution;
  (4) baking potassium hydrogen phthalate in an oven at 105° C. for 10-12 hours and then placing the potassium hydrogen phthalate in a dryer for cooling for at least 1 hour;
  (5) with the potassium hydrogen phthalate obtained above as solute and distilled water as solvent, preparing a potassium hydrogen phthalate solution in an automatic potentiometric-titrator by weighing an appropriate amount of the potassium hydrogen phthalate obtained above and added with the distilled water, the result of weighing the potassium hydrogen phthalate being as precise as 0.1 mg;
  (6) dripping the titrative alkali-ethanol solution in the potassium hydrogen phthalate solution by using the automatic potentiometric-titrator to achieve a first end point, and computing concentration of the titrative alkali-ethanol solution;
  (7) repeating Step (6) twice and computing an average of the concentrations of the titrative alkali-ethanol solution for the three titrations in order to determine an actual concentration of the titrative alkali-ethanol solution;
  (8) providing an acid mixture of aluminum etchant, which includes an acid mixture sample comprising nitric acid, phosphoric acid, and acetic acid and adding a first solvent and a second solvent in the acid mixture sample and uniformly stirring to obtain an acid mixture solution of aluminum etchant, the first solvent being monohydric alcohol and the second solvent being diol;
  (9) dripping the titrative alkali-ethanol solution in the acid mixture of aluminum etchant by using the automatic potentiometric-titrator to achieve a first, a second and a third equivalence points and computing concentrations of nitric acid, phosphoric acid, and acetic acid contained in the acid mixture of aluminum etchant according to amounts of consumption of the titrative alkali-ethanol solution when the first, second, and third equivalence points occur by applying the following formulas:

$m_{HNO3}\% = V_{EP1} \times C \times M_{HNO3}/m;$ $m_{H3PO4}\% = V_{(EP2-EP1)} \times C \times M_{H3PO4}/m;$ and $m_{HAC}\% = V_{(EP3-EP2)} \times C \times M_{HAC}/m;$ wherein C is concentration of the alkali-ethanol solution; $V_{EP1}$ is the volume of the alkali-ethanol solution consumed at the first equivalence point; $V_{(EP2-EP1)}$ is difference between volumes of the alkali-ethanol solution consumed at the second and the first equivalence points; $V_{(EP3-EP2)}$ is difference between volumes of the alkali-ethanol solution consumed at the third and the second equivalence points; m represents the mass of the acid mixture of aluminum etchant used; and M is molar mass of each one of the acids; and
  (10) repeating Step (9) twice and computing averages of the concentrations of nitric acid, phosphoric acid, and acetic acid contained in the acid mixture of aluminum etchant for the three measurements to determine actual concentrations of nitric acid, phosphoric acid, and acetic acid;
  wherein the alkali comprises potassium hydroxide having an analytical reagent (AR) concentration greater than or equal to 85%;
  wherein the monohydric alcohol comprises methanol or ethanol;
  wherein the diol comprises glycol, 1,2-propanediol, or 1,4-butanediol;
  wherein the first solvent and the second solvent have a volume ratio therebetween of 3:1-3:5;
  wherein a sum of volumes of the first and second solvents is 200-400 times of mass of the acid mixture sample of aluminum etchant;
  wherein in Step (1), the alkali-ethanol solution has a concentration of 1 mol/L;
  wherein in Step (2), the alkali-ethanol solution is set still and precipitated for 30 days; and
  wherein in Step (4), potassium hydrogen phthalate is baked for a period of 12 hours.

* * * * *